US007494494B2

(12) United States Patent
Stoianovici et al.

(10) Patent No.: US 7,494,494 B2
(45) Date of Patent: Feb. 24, 2009

(54) CONTROLLABLE MOTORIZED DEVICE FOR PERCUTANEOUS NEEDLE PLACEMENT IN SOFT TISSUE TARGET AND METHODS AND SYSTEMS RELATED THERETO

(75) Inventors: Dan Stoianovici, Baltimore, MD (US); Gabor Fichtinger, Kensignton, MD (US); Richard Matthew Wiard, Fremont, CA (US); Ioan Julian Iordachita, Craiova (RO); Louis Litchfield Whitcomb, Baltimore, MD (US); Russell H. Taylor, Saverna Park, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/943,751

(22) Filed: Aug. 30, 2001

(65) Prior Publication Data
US 2002/0111634 A1    Aug. 15, 2002

Related U.S. Application Data

(60) Provisional application No. 60/228,993, filed on Aug. 30, 2000.

(51) Int. Cl.
*A61B 19/00* (2006.01)
(52) U.S. Cl. ............... 606/129; 600/566; 600/568
(58) Field of Classification Search ........... 606/80, 606/96, 188, 129, 130, 74; 600/566, 567, 600/568; 74/490.01, 490.03–490.06
See application file for complete search history.

(56) References Cited

U.S. PATENT DOCUMENTS
5,647,373 A * 7/1997 Paltieli ............... 600/567
(Continued)

FOREIGN PATENT DOCUMENTS
WO    WO 98/36688    *  8/1998 ............... 600/427

OTHER PUBLICATIONS

Loser, et al., "A New Robotic System for Visually Controlled Percutaneous Interventions under CT Fluoroscopy", Lecture Notes in Computer Science 1935, Medical Image Computing and Computer-Assisted Intervention MICCAI 2000, Third International Conference, Pittsburgh, PA, USA, Oct. 2000.

(Continued)

*Primary Examiner*—Kevin T Truong
*Assistant Examiner*—Victor X Nguyen
(74) *Attorney, Agent, or Firm*—Edwards Angell Palmer & Dodge LLP; Peter F. Corless; Lisa Swiszcz Hazzard (57) ABSTRACT

Featured is an apparatus that places or locates a proximal end portion of a penetrating member in a target area of a body. Such an apparatus or needle driver is particularly suited for locating a percutaneous needle in a soft tissue target area of a body particularly a body having inhomogeneous soft tissues. The apparatus includes a first arm that is configured and arranged so as to support a distal portion of the penetrating member and a first drive mechanism that is coupled to the first arm. The first drive mechanism is configured and arranged to move or translate the first arm from an initial position to any of a number of other positions that are spaced from the initial position and correspondingly translate the proximal end portion of the penetrating member. In another embodiment, the first arm also rotatably supports the penetrating member and the apparatus further includes a second drive mechanism coupled to the penetrating member distal portion and which is configured an arranged to rotate the penetrating member about the translational axis.

57 Claims, 7 Drawing Sheets

U.S. PATENT DOCUMENTS

| | | | | |
|---|---|---|---|---|
| 5,660,185 A | * | 8/1997 | Shmulewitz et al. | 600/562 |
| 5,695,500 A | * | 12/1997 | Taylor et al. | 606/130 |
| 5,766,126 A | | 6/1998 | Anderson | |
| 5,820,623 A | * | 10/1998 | Ng | 606/1 |
| 6,080,181 A | * | 6/2000 | Jensen et al. | 606/205 |
| 6,086,544 A | * | 7/2000 | Hibner et al. | 600/568 |
| 6,106,511 A | * | 8/2000 | Jensen | 606/1 |
| 6,251,121 B1 | * | 6/2001 | Saadat | 606/180 |
| 6,337,994 B1 | * | 1/2002 | Stoianovici et al. | 600/547 |
| 6,400,979 B1 | * | 6/2002 | Stoianovici et al. | 600/427 |
| 6,786,896 B1 | * | 9/2004 | Madhani et al. | 606/1 |

OTHER PUBLICATIONS

Bzostek, et al., "An Automated System for Precise Percutaneous Access of the Renal Collecting System", Lecture Notes in Computer Science 1205, CVRMed-MRCAS' 97, First Joint Conference, Grenoble, France, Mar. 1997.

Masamune, et al., "A Newly Developed Stereotactic Robot with Detachable Drive for Neurosurgery", Lecture Notes in Computer Science 1496, Medical Image Computing and Computer-Assisted Intervention-MICCAI' 98, First International Conference, Cambridge, MA, USA, Oct. 1998.

Kumar, et al., "Performance of Robotic Augmentation in Microsurgery-Scale Motions", Lecture Notes in Computer Science 1679, Medical Image Computing and Computer-Assisted Intervention-MICCAI' 99, Second International Conference, Cambridge, UK, Sep. 1999.

Kobayashi, et al., "A New Laparoscope Manipulator with an Optical Zoom", Lecture Notes in Computer Science 1496, Medical Image Computing and Computer-Assisted Intervention-MICCAI' 98, First International Conference, Cambridge, MA, USA, Oct. 1998.

Stoianovici, et al., "An Efficient Needle Injection Technique and Radiological Guidance Method for Percutaneous Procedures", Lecture Notes in Computer Science 1205, CVRMed-MRCAS' 97, First Joint Conference, Grenoble, France, Mar. 1997.

Schreiner, et al., "A System for Percutaneous Delivery of Treatment with a Fluoroscopically-Guided Robot", Lecture Notes in Computer Science 1205, CVRMed-MRCAS' 97, First Joint Conference, Grenoble, France, Mar. 1997.

Bzostek, et al., "A Testbed System for Robotically Assisted Percutaneous Pattern Therapy", Lecture Notes in Computer Science 1679, Medical Image Computing and Computer-Assisted Intervention-MICCAI' 99, Second International Conference, Cambridge, UK, Sep. 1999.

* cited by examiner

CONTROLLABLE MOTORIZED DEVICE FOR PERCUTANEOUS NEEDLE PLACEMENT IN SOFT TISSUE TARGET AND METHODS AND SYSTEMS RELATED THERETO

This application claims the benefit of U.S. Provisional Application Ser. No. 60/228,993 Aug. 30, 2000, the teachings of which are incorporated herein by reference.

STATEMENT OF GOVERNMENT INTEREST

Funding for the present invention was provided in part by the Government of the United States by virtue of Grant No. EEC9731478 by the National Science Foundation. Thus, the Government of the United States has certain rights in and to the invention claimed herein.

FIELD OF INVENTION

The present invention relates to methods, systems and devices for percutaneous surgery and more particularly to a controllable, motorized device for percutaneous needle placement in a soft tissue target including systems and methods related thereto.

BACKGROUND OF THE INVENTION

As an alternative to traditional surgical techniques or methodologies, percutaneous surgery has been found to significantly reduce morbidity and post-operative recovery time. A fundamental problem in clinical delivery of percutaneous therapy and needle biopsy is precise placement of the percutaneous needle in inhomogenous soft tissue. The accuracy of delivery is dependent upon both accurate targeting and on the precise driving of the needle on the target. In conventional systems and methods, the targeting accuracy exceeds and often greatly exceeds the driving accuracy that can be achieved. Furthermore, a wide spectrum of treatment methods require that the percutaneous needle be held firmly in the target location for a considerable period of time while the patient is in repiratory, cardiac and muscular motion.

This need for accurate delivery initially required that the surgeon performing the procedure have an extensive amount of experience and skill, however, there were shortcomings with such procedures. For example, then existing radiological image guidance techniques could not provide effective three-dimensional information to the surgeon regarding needle insertion. Consequently a number of robotic systems were proposed to assist in placement of the needle. Such robotic system solutions are found in "Intraoperative Imaging Guidance for Keyhole Surgery Methodology and Calibration," Potamianos, P. Davies, B. L. and Hubbard, R. D., Proceedings for the First International Symposium on Medical Robotics and Computer Assisted Surgery, Pittsburgh, Pa., pp. 98-104 (1994); "Intraoperative Imaging Guidance for Keyhole Surgery Methodology and Calibration", Potamianos, P. Davies, B. L. and Hubbard, R. D., Proceedings for the First International Symposium on Medical Robotics and Computer Assisted Surgery, Baltimore Md., pp. 156-164 (1995); "An Automated System for Precise Pecutaneous Access of the Renal Collection System", Bzostek, A., Schreiner, S., Barnes, A. C., Cadeddu, J. A., Roberts, W. Anderson, J. H., Taylor, R. H. and Kavoussii, L. R. submitted for review to the Proceedings of the First Joint Conference of CVRMed and MRCAS, Grenoble France (1997) and PCT Publication No. WO 989/3688, published Aug. 27, 1998. A number of other robotics systems and methods for use in connection with surgical procedures, including sub-systems, methods and/or device related thereto, are found in U.S. Pat. Nos. 5,086,401; 5,299,288; 5,408,409; 5,279,309; 5,695,500; 5,630,431; 5,445,166; 5,402,801; 5,950,629; 5,976,156; 5,417,210; 5,572,999; 5,749,362; and 5,397,323.

Conventional needle drivers for percutaneous therapies typically utilize a friction transmission to achieve motion along the translational axis or idealized travel path, translational motion, to guide a needle into a soft tissue target. The translational axis is the axis along which the percutaneous needle generally travels to the soft tissue target. Such conventional friction transmission needle drivers, however, have a few shortcomings.

A frictional transmission has limited accurate encoding to track the translational position of the needle. For example, needle slippage results in loss of encoding, which in turn results in loss of accurate positioning of the needle in the translation axis. Needle slippage occurs when the force experienced by the needle is greater than the product of the preload contact force and the dynamic coefficient of friction. Needle deviation from the planned target also can occur because of needle deflection, organ deformation and respiratory, cardiac or muscular motion. Needle deflection can result from high needle insertion forces, the forces necessary for penetration into the tissue target, which is greatest at the initial point of entry. Needle deflection is a particular concern due to tissue inhomogeneities which in effect creates more of entry points for the needle as it traverses within the body.

It thus would be desirable to provide an improved new device, apparatus, system and related methods so a needle or other penetrating member can be accurately driven into an identified target in a soft tissue target and also retain encoding. It would be particularly desirable to provide such a device, apparatus, system and method that reduces or minimizes insertion forces in comparison to prior art devices and methods while the needle is being translated. It also would be desirable to provide such a device, apparatus, system and method that would lead to more accurate final positioning of the needle as compared to prior art devices. Further, it would be desirable to provide a device, apparatus, system and method providing more accurate encoding and tracking of translational needle position as compared to prior art device and methods. Such devices, apparatuses, systems preferably would be simple in construction and less costly than prior art devices and such methods would not significantly increase the complexity of surgical techniques to utilize the device, apparatus or system.

SUMMARY OF THE INVENTION

The present invention features an apparatus that places or locates a proximal end portion of a penetrating member in a target area of a body. Such an apparatus or needle driver is particularly suited for locating a percutaneous needle in a soft tissue target area of a body particularly a body having inhomogenous soft tissues. Also featured are systems that use such an apparatus as well as methods related to the apparatus and systems.

According to one aspect of the present invention, such an apparatus includes an arm, a first arm, that is configured and arranged so as to support the penetrating member, a distal portion of the penetrating member and a drive mechanism or drive transmission assembly, a first drive mechanism, that is coupled (i.e., mechanically coupled) to the first arm. The first drive mechanism is configured and arranged so as to move or translate the first arm from an initial position to any of a number of other positions that are spaced from the initial position and correspondingly translate the proximal end portion of the penetrating member. One of these other positions corresponds to locating the proximal end portion of the penetrating member in the target area.

In a further embodiment, the first arm also is configured and arranged to rotatably support the penetrating member and the apparatus further includes another drive mechanism or drive transmission assembly, a second drive mechanism, that is coupled to the penetrating member distal portion and which is configured an arranged so as to rotate the penetrating member about a long axis thereof, the translational axis. In a more particular embodiment, the second drive mechanism also is coupled to the first arm.

In another further embodiment, the apparatus further includes a controller that is configured and arranged so as to selectively control the first and second drive mechanisms. In more particular embodiments, the controller is configured and arranged to include a plurality or more of pre-established protocols to implement any one of a plurality or more of techniques for driving the proximal portion of the penetrating member from the initial position to the final position. In one specific embodiment, the surgical personnel manually make the change from one pre-established protocol to another pre-established protocol manually. In another specific embodiment the change from one pre-established protocol to another pre-established protocol is effected automatically by the controller according to a preprogrammed sequence or responsive to receipt of external signals.

Such techniques or protocols include both translating and rotating the penetrating member proximal portion when the proximal end of the penetrating member (e.g., needle) is proximal the barrier, membrane or the like defining the interface or outermost surface of the body to be penetrated (e.g., the point of entry). This includes the barrier or interface defining each layer of a body having an inhomogeneous structure. In the case of inhomogeneous tissue layers, the interface defining the boundary between the discrete tissue layers. Another exemplary technique is repetitively translating the penetrating member in a back and forth motion like a hammering motion. Such repetitive translating is done in conjunction with rotation of the penetrating member or without rotation of the penetrating member. The above-described protocols/techniques are illustrative/exemplary of a few protocols or techniques and thus should not be considered exhaustive of all the possible scenarios for operating the first and second drive mechanisms.

According to a second aspect of the present invention such an apparatus further includes another arm, a second arm, that is spaced from the first arm and wherein the first drive mechanism as it translates the first arm from the initial position also moves the first and second arms with respect to each other. More particularly, the first arm translates or moves towards the second arm. In further embodiments, the second arm includes a guide mechanism in which is received the penetrating member. The guide mechanism is configured and arranged so as to guide and maintain the penetrating member along the travel path (e.g., translational axis) desired for traversing the body from the entry point or location to the target area.

According to a third aspect of the present invention, the first arm is further configured and arranged to releasably support the penetrating member distal portion and the second arm guide portion releasably receives the penetrating member therein. In a more particular embodiment, each of the first and second members is further configured and arranged so as to include a releasable segment that is releasably secured to the other portion of the arm. In more particular embodiments, the apparatus further includes a release-grasp mechanism that is configured and arranged to secure the releasable segment to its arm and to de-secure the release segment upon some action by the surgical personnel. In a more specific embodiment, such de-securing occurs automatically when certain conditions (e.g., power failure) is determined to exist.

According to a fourth aspect of the present invention, the apparatus further includes the penetrating member, which penetrating member is configured an arranged so as to perform any of a number of techniques, protocols, surgical techniques or therapeutic techniques. These include but are not limited to injection of therapeutic agents in the target area, location an imaging device in the target area, biopsy, injection of a material in the target area to improve imaging of the target area and surround areas, and location of a device (e.g., RF or ultrasound transmitter) in the target area to perform a procedure, for example tissue ablation and breaking up stones.

According to a fifth aspect of the present invention, the apparatus further includes a sensing mechanism for sensing any one of a number of physical parameters (e.g., forces, vibrations) and for coupling the output of each of these sensors to the controller. In more particular embodiments, the controller is configured to give at least one of an auditory or visual que or message to the surgical personnel indicating that a certain condition might be present, for example a tissue wall or calcification, such that the personnel can determine if the driving protocol for the penetrating member should be adjusted (e.g., increase or decrease rotational speed) or changed (e.g., stop rotating and start a hammering translation motion).

Further, the controller is further configured and arranged so that it selectively controls the operation of the first and second drive mechanisms responsive to such signals. For example, the controller is configured and arranged to stop the drive mechanisms when a condition(s) suggestive or indicative of an anomalous condition is detected. Also the controller can be configured so as to provide an auditory and/or visual alarm of when the anomalous condition is detected.

According to a more particular aspect of the present invention, the apparatus is configured and arranged for encodable placement of a percutaneous needle in a soft tissue target, such as that of a human body.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Referring now to the various figures of the drawing wherein like reference characters refer to like parts, there is shown in FIGS. 1-5 various views of a penetrating member driver 100 according to the present invention particularly configured and arranged for driving a penetrating member, such as a needle 50, into a target area of soft tissue of a body. These figures also illustrate various in process configurations of the penetrating member driver 100 as well as illustrating its use in connection with a member 60 of any of a number of manual, motorized or robotic targeting apparatuses or systems as is known to those skilled in the art. In use these manual, motorized or robotic targeting apparatuses or systems are operated so the needle 50 axis being held in the penetrating member driver 100 is positioned and oriented so that it points at the entry point of the body and also so that the needle is oriented such that it translates along the translational axis to the target area. Such apparatuses and systems are more particularly identified elsewhere herein, the teachings of which are incorporated herein by reference.

The needle 50 is any of a number of penetrating members known to those skilled in the art, and more particularly includes any of a number of percutaneous needles known to those skilled in the art. As more specifically described hereinafter each needle 50 also is configured so as to include a gear member 184 (see FIGS. 2-3) that is attached to the exterior of the needle using any of a number of techniques known to those skilled in the art at a predetermined axial location. In use, a stylet also may be inserted into the lumen of the needle 50, so as to provide axial support and so as to provide an end detail more appropriate for minimizing trauma at entry points and minimizing the forces required for penetrating the tissue boundary at the entry point, for example a diamond end detail.

The penetrating member driver 100 includes a housing 110, first and second arms 120, 140, a motorized translation transmission assembly 160, a motorized rotation transmission assembly 180 and a latch assembly 190. The housing 110 is configured and arranged so as to provide structural support to the first and second arms 120, 140, the motorized translation transmission assembly 160 and the latch assembly 190. In the illustrated embodiment, the housing also substantially encloses the motorized translation transmission assembly 160, motorized rotation transmission assembly 180 and latch assembly 190. The configuration, thickness, and materials of the housing 110 are selected such that it can provide the required structural support while minimizing its capability for being a source of contaminants to the medical procedure penetrating member driver 100 is being used in conjunction with. In an illustrative embodiment, the housing 110 is made from aluminum.

In the illustrated embodiment, the first arm 120, where the translation arm, includes two parts, the support part 122 and the cantilevered part 124, where the cantilevered part also includes a releasable segment 126. The support part 122 is configured and arranged to receive and secure the cantilevered part 124 in a pocket 123 formed therein and to support the drive motor 182 for the motorized rotation transmission assembly 180. The pocket 123 also provides a pathway for coupling the motorized rotation transmission drive motor 182 to the drive gear 186.

The first arm support part 122 also is configured and arranged so as to include two through apertures therein arranged general perpendicular to the pocket 123. One aperture is configured and arranged to receive therein the ball screw coupler 166 of the motorized translation transmission assembly 160 and to secure the ball screw coupler therein such that it cannot rotate. The other aperture is configured and arranged to receive and secure therein the guide member 178 of the motorized translation transmission assembly 160. The inter-relationship between the first arm, these parts and the motorized translation transmission assembly in general is discussed below.

The configuration, thickness, and materials of the first arm support part 122 are selected such that it can provide the required structural support while minimizing its capability for being a source of contaminants to the medical procedure the penetrating member driver 100 is being used in conjunction with. The support part 122 also is configured and arranged so that any external moment loading, imposed on the first arm 120 is passed onto the linear guide 172 without distortion of the structure making up the support part. Because it is out of the field of view for the target area, the materials of the support part 122 need not be lucent to the particular type of source used for imaging, for example the materials need not be radiolucent (i.e., lucent to x-rays). In an illustrative embodiment, the first arm support part 122 is made from aluminum however other materials are contemplated for use.

The cantilevered part 124 extends outwardly from the support part 122 and the housing 110 and has a length such that the penetrating member 50 is located well away from the housing and support part so that the housing and support part are not located in the field of view for the target area or the point of entry. The cantilevered part 124 also is configured and arranged so that it has a pocket 132 therein that runs lengthwise. This cantilevered part 124 also is configured and arranged so that the gear drive 186 is rotatably disposed at a distal end of the pocket 132 and so that the drive belt 190 passes therethrough to mechanically couple the gearhead 168 and the drive gear. The gear drive 186 also is located or positioned such that the gear member 184 and the gear drive are in mechanical engagement with each other when the releasable segment 126 is secured to the first arm cantilevered part 124. Additionally, the cantilevered part 124 is configured and arranged such that when the first arm 120 translates in a direction 102 towards or away from the second arm 140, the needle 50 or penetrating member is correspondingly translated at the same time.

For purposes of releasably securing the needle 50 to the first arm 120, the cantilevered part 124 includes a releasable segment 126, which segment includes a catch arm 128 that extends outwardly from a portion of a surface. When the releasable segment is secured to the rest of the cantilevered part 124, the catch arm 128 is located in a channel 134 that runs lengthwise within the cantilevered part 124 and continues through the support part 122. When in this secured condition, a notch 130 or other surface artifact of the catch arm 128 is located proximal to and is put into engagement with a latch finger 192 of the latch assembly 190.

The configuration, thickness, and materials for the first arm, cantilevered part 124 are selected such that it can provide the required structural support for the needle 50 and so that translational motion of the first arm 120 is correspondingly imparted to the needle. The cantilevered part 124 also is configured and arranged so that any external moment loading, imposed on the first arm 120 is passed onto the support part 122 and thence onto the linear guide 172 without distortion of the structure making up the first arm. Because the cantilevered part 124 is in the field of view for the target area, the materials of the cantilevered part are selected so as to be lucent to the particular type of source used for imaging, for example the materials are radiolucent (i.e., lucent to x-rays). In an illustrative embodiment, the first arm cantilevered part 124 is made from a plastic such an acrylic plastic however other radiolucent materials are contemplated for use.

In the illustrated embodiment, the second arm 140, also the fixed arm includes two parts, the support part 142 and the cantilevered part 144, where the cantilevered part also includes a release segment 146. The second arm support part 142 is configured and arranged to receive and secure the cantilevered part 144 in a pocket 143 formed therein. The second arm support part 142 also is secured to the housing bottom 112 using any of a number of techniques known to those skilled in the art including welding, brazing, adhesively and mechanically (e.g., nuts, screws, bots, etc.).

The configuration, thickness, and materials for the second arm support part 142 are selected such that it can provide the required structural support while minimizing its capability for being a source of contaminants to the medical procedure the penetrating member driver 100 is being used in conjunction with. The second arm support part 142 also is configured and arranged so that any external moment loading, imposed on the second arm 120 is passed onto the housing 110. Because it is out of the field of view for the target area, the materials of the support part 142 need not be lucent to the particular type of source used for imaging, for example the materials need not be radiolucent (i.e., lucent to x-rays). In an illustrative embodiment, the second arm support part 142 is made from aluminum however other materials are contemplated for use.

The cantilevered part 144 extends outwardly from the support part 142 and the housing 110 and has a length such that the penetrating member 50 is located well away from the housing and support part so that the housing and support part are not located in the field of view for the target area or the point of entry. The cantilevered part 144 also is configured and arranged so that it includes a guide 152 for the penetrating member/needle 50. The guide 152 has a through aperture and is sized so it slidably receives the penetrating member/needle 50 therein. The guide 152 also is disposed and located at a distal end portion of the second arm 140 and located so that the penetrating member/needle 50 extends between the first arm 120 and the second arm 140 such that the penetrating member/needle 50 will translate along a predetermined axis, the translational axis, and so the gear member 184 is maintained in mechanical engagement with the drive gear 186.

For purposes of releasably securing the needle 50 to the second arm 140, the cantilevered part 144 includes a releasable segment 146, which segment includes a catch arm 148 that extends outwardly from a portion of a surface. When the releasable segment is secured to the rest of the cantilevered part 144, the catch arm 148 is located in a channel 134 that runs lengthwise within the cantilevered part 144 and continues through the support part 142. When in this secured condition, a notch 150 or other surface artifact of the catch arm is located proximal to and is put into engagement with a latch finger 192 of the latch assembly 190.

The configuration, thickness, and materials of the second arm, cantilevered part 144 are selected such that it can provide the required structural support for the anticipated mechanical loadings and intended service. The cantilevered part 144 also is configured and arranged so that any external moment loading, imposed on the second arm 140 is passed onto the support part 142 and thence onto the housing bottom 112 without distortion of the structure making up the second arm. Because the cantilevered part 144 is in the field of view for the target area, the materials of the cantilevered part are selected so as to be lucent to the particular type of source used for imaging, for example the materials are radiolucent (i.e., lucent to x-rays). In an illustrative embodiment, the cantilevered part 144 is made from a plastic such as an acrylic plastic however other radiolucent materials are contemplated for use.

The motorized translation transmission assembly 160 includes a motor 162, a ball screw 164, interconnecting gearing 163, a ball screw coupler 166, bearings 168, and a linear guide 172. The motor 162 is any of a number of types of fractional horsepower, bi-directional drive motors known in the art including electrical motors, pneumatically powered motors and hydraulically powered motors. In an exemplary illustrative embodiment, the motor is a bi-directional electrical motor. Preferably, the motor 162 is an encoded type.

The interconnecting gearing 163 that mechanically couples the motor 162 to the ball screw 164 is configured and arranged so that the motor rotates the ball screw with very little to, and including, no slippage therebetween. In an exemplary embodiment, the interconnecting gearing 163 includes a planetary gear reduction head, having a 4:1 reduction, so that a maximum translational speed can be developed.

The ball screw 164 also is mechanically interconnected to the ball screw coupler 166 secured in the first arm support part 122. The ball screw coupler 166 is any of a number of devices known to those skilled in the art, which develop linear motion or motion in one direction generally parallel to the axis of rotation, responsive to rotational motion of a member rotating therein. Thus, when the ball screw 164 is rotated within the ball screw coupler 166 responsive to the operation of the motor 162, the ball screw coupler in turn causes the first arm 120 to move in a direction 102 towards or away from the second arm 140 responsive to the rotation and the direction of rotation of the ball screw. The ends of the ball screw 164 also are supported by the bearings 168 to minimize the frictional losses in the rotation power translation.

This configuration and arrangement of the motorized translation transmission assembly 160 yields a translation drive that is essentially slipless in the bi-directional tranalational axis, which results in a drive capable of providing accurate and controllable encoding. The ball screw 164 also offers anti-backlash between the motor and the first arm, for accurate and controllable position encoding. In a particular embodiment, a low screw pitch diameter was selected for the ball screw 164 so that the motor 162 will experience relatively constant force feedback when the needle passes through different regions of anisotropic (i.e., inhomogeneous) soft tissue, and patient movements such as organ and respiration. Because there is no slippage and no loss of encoding, the penetrating member/needle 50 can be released from the penetrating member driving device 100 of the present invention without loss of encoding. Consequently, the penetrating member/needle 50 can be re-affixed to the penetrating member device 100 so that the end portion again lies within the same target area.

The linear guide 172 includes a rod member 174, a track 176, a sliding member 178, a mount 173 for the rod member and a coupling mechanism 175. The sliding member 178 is configured and arranged so a portion thereof slidably engages the track 176. The sliding member 178 also is configured and arranged so another portion thereof is secured to the first arm 120. The coupling mechanism 175 is secured to the sliding member 178 and overlays the rod member 174 such that the rod member is slidably received within the coupling mechanism and so that the rod member is slidably coupled with the sliding member. In this way, as the first arm 120 translates responsive to the rotation of the gear screw 164, motion in directions other than direction 102 of translation by the first arm is suppressed by the sliding engagement between the sliding member 178 and the track 176 and by the sliding coupling of the sliding member and the rod member 176. Similarly, external moment loadings being imposed on the first arm 120 are communicated to and suppressed by the linear guide 172. The linear guide 172 also can further include one or more mechanical stops 177 to restrain the translational motion of the first arm 110.

The motorized rotational transmission assembly 180 includes a motor 182, the gear member 184, a drive gear 186, a gearhead 188 and a drive belt 189. The motor 182 is any of a number of types of fractional horsepower, bi-directional drive motors known in the art including electrical motors, pneumatically powered motors and hydraulically powered motors. In an exemplary illustrative embodiment, the motor is a bi-directional electrical motor. This motor 182 need not be of the encoded type.

The gearhead 188 is coupled to the motor 182 and to the drive belt 189. The drive belt 189 in turn is coupled to the drive gear 186 so that the operation of the motor causes the rotation of the drive gear. As indicated above, when assembled, the drive gear 186 is in mechanical engagement with the gear member 184 that is affixed to the penetrating member/needle 50. Consequently the penetrating member/needle 50 rotates in a direction 104 in a clockwise or counterclockwise direction responsive to the direction of rotation of the motor 182.

In a more particular embodiment, the gear member 184 for the penetrating member/needle 50 is preferably sized so that it can be adapted for use with penetrating members/needles having a wide range of different diameters or different gauges. More specifically, the inner hub of the gear member 184 has a diameter generally larger than the diameters of penetrating members/needles 50 for use in the present invention. In this way, the outer diameter of the gear member 184 does not change for different size needles and thus there is no change in the gear-contact dimension for the gear member 184. Consequently, the same radiolucent first arm 120 and motarized rotation transmission assembly 180 is useable for penetrating members/needles 50 being of different diameters or gauges. In an illustrative embodiment, the space between the gear member inner hub is filled with a material such as epoxy so as to secure the gear member 184 to the penetrating member/needle 50 and to fill in any open space therebetween.

This drive gear 186 to gear member 184 arrangement yields a gear transmission for the penetrating member/needle 50 having little preload force and which provides bi-directional rotational motion and zero slippage and backlash. The drive gear 186, the gear member 184 and the drive belt are constructed of a material appropriate for the intended structural loadings and also lucent to the imaging source as also discussed above for the first and second arm cantilevered parts 124, 144.

In an exemplary embodiment, the gearhead 188 is a planetary gearhead which is compact in size and allows overall gear reduction to be achieved at the motor location. The drive belt 189 is any of a number of belts known to those skilled in the art and in an exemplary embodiment is an o-ring pulley belt. However, other types and configurations of drive belts, such as toothed drive belts are contemplated for use in the present invention otherwise consistent with the teachings of the present invention.

Figure 5:
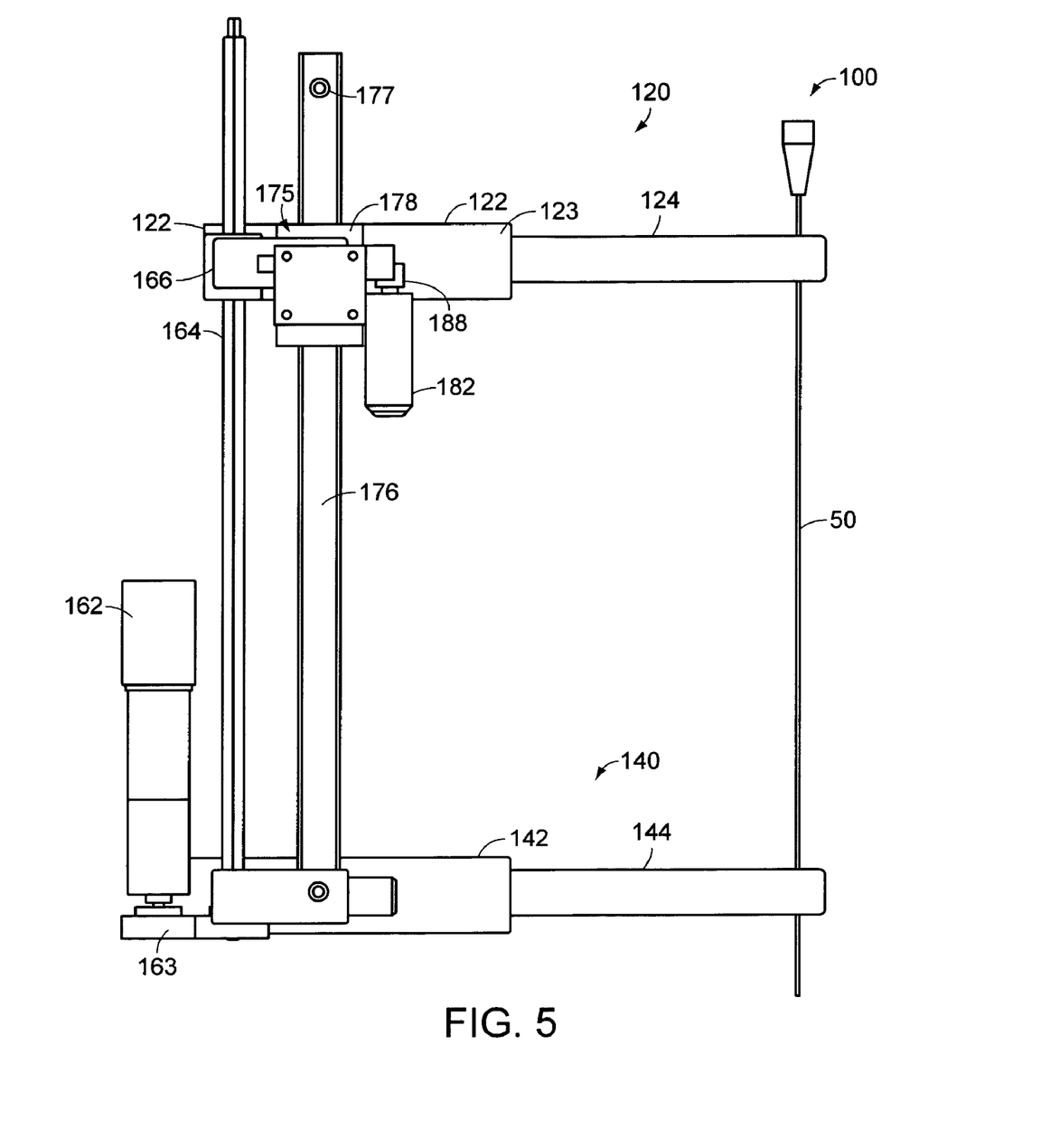
FIG. 5 is a side view of an alternative penetrating member driver.

There is shown in FIG. 5 and alternative arrangement for the rotation drive motor 182. In this illustrative arrangement, the motor 182 is located so it extends below the first arm 120. In the other illustrative embodiments the motor 182 is illustrated as extending above the first arm 120. It should be recognized that this orientations of the motors 162, 182 for the motorized translation and rotation transmission assemblies 160, 180 are illustrative as the motors can be adapted so as to be arranged in other configurations otherwise consistent with the teachings of the present invention.

Each latching assembly 190 includes a latch finger 192, a spring 194 or other biasing mechanism and a solenoid 196 that controls the actuation and de-actuation of the latch finger. As indicated above, when the penetrating member driver 100 is in its assembled configuration, the catch arm 128,148 of the first and second arm releasable segments 126, 146 are inserted into the channel 134 and the notch 130, 150 in each catch arm is put into engagement with the latch finger 192. The latch fingers 192 are designed such that when the solenoid 196 is actuated, the latch fingers will engage and remain engaged with the notch 130, 150.

When the solenoid is de-actuated the latch fingers 192 are released and biased so as to disengage from the notch 130, 150 thereby releasing each catch arm 128, 148. Such de-activation can be the result of the actuation of a manual switch by the surgical personnel, responsive to a signal from a sensor, or responsive to the loss of power to the motors 162, 182 (e.g., loss of electricity, pneumatic pressure or hydraulic pressure). Thereafter, a spring 194 acts on each of the catch arms 128, 148 causing the catch arm to be moved outwardly and so that the corresponding releasable segment 126, 146 is biased away from the corresponding cantilvered part 124, 144 as is more particularly shown in FIG. 3.

Figure 1:
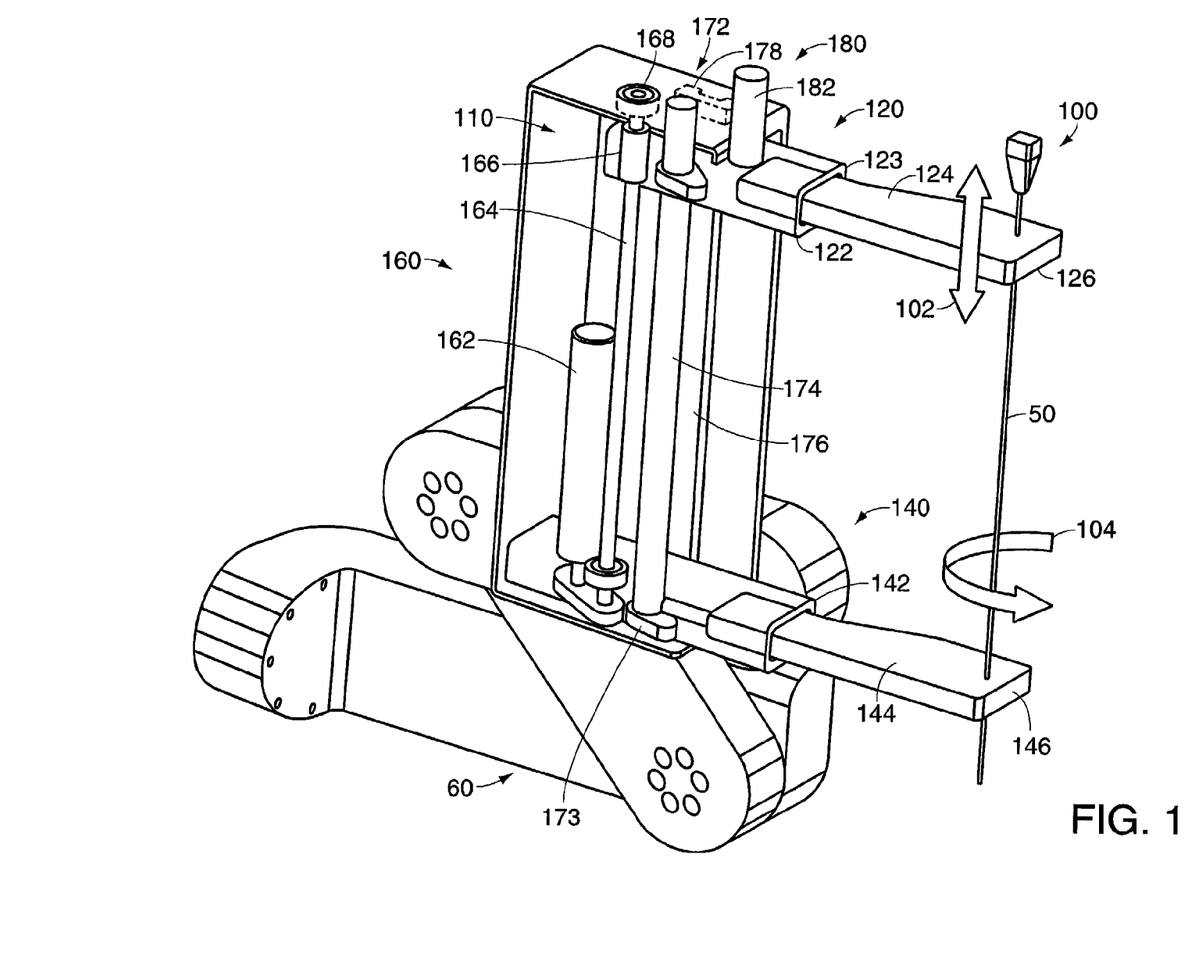
FIG. 1 is a perspective view of a penetrating member driver according to the present invention on a member of a targeting apparatus/system.
Figure 2:
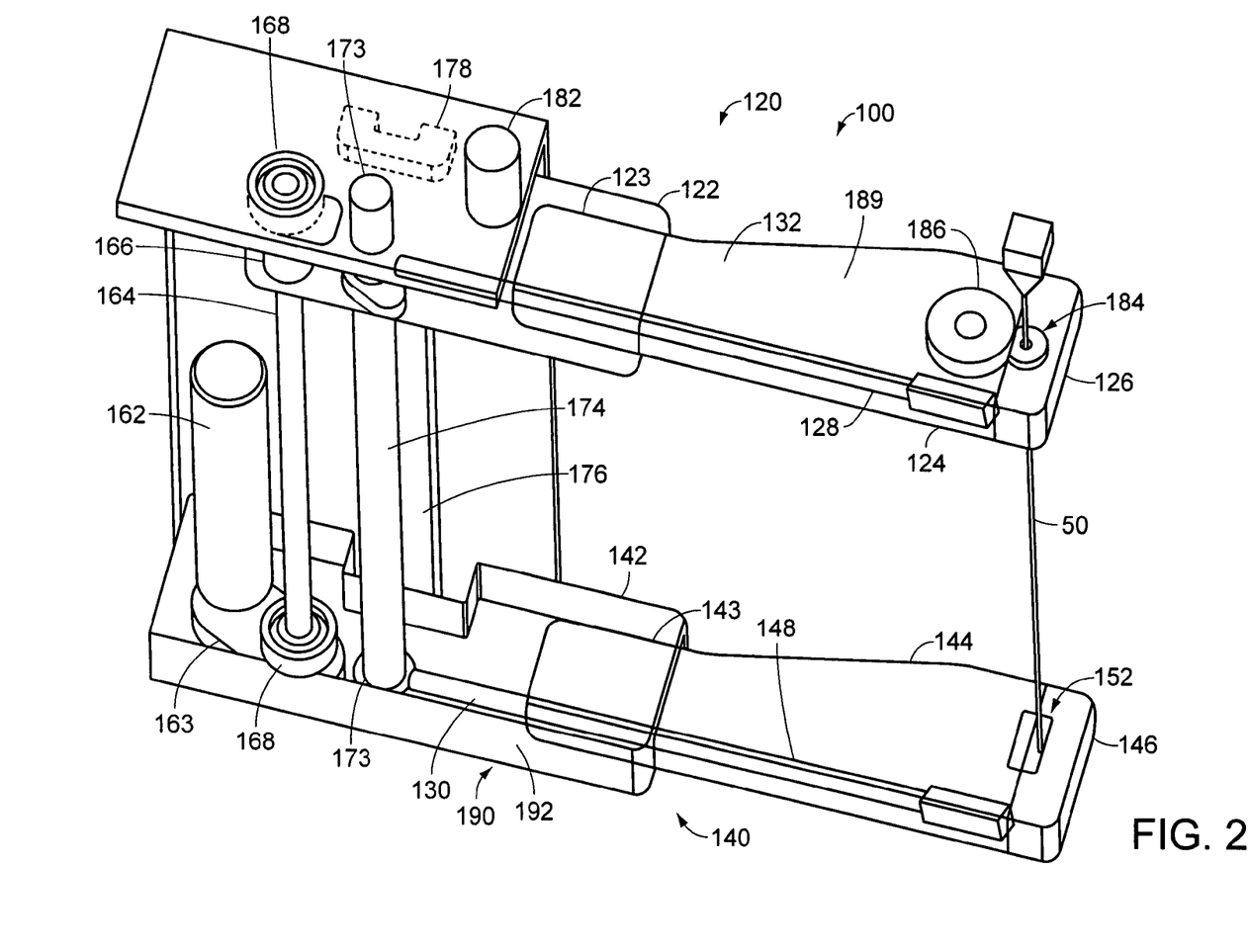
FIG. 2 is a perspective view of the penetrating member driver of FIG. 1 with sides of the housing removed for clarity.
Figure 3:
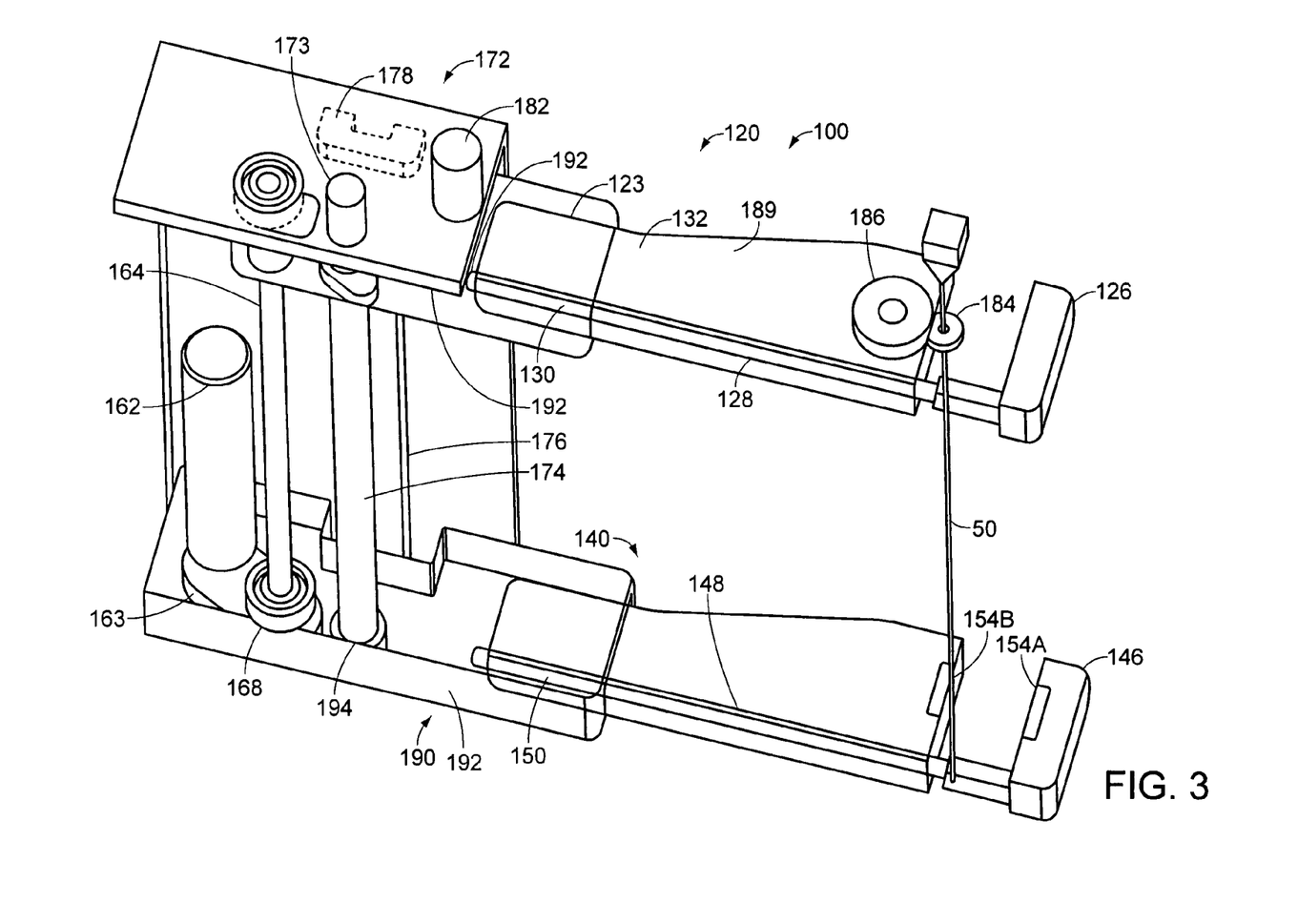
FIG. 3 is a perspective view of the penetrating member driver of FIG. 2 where the release-grasp mechanism is actuated to de-secure the release segment.
Figure 4:
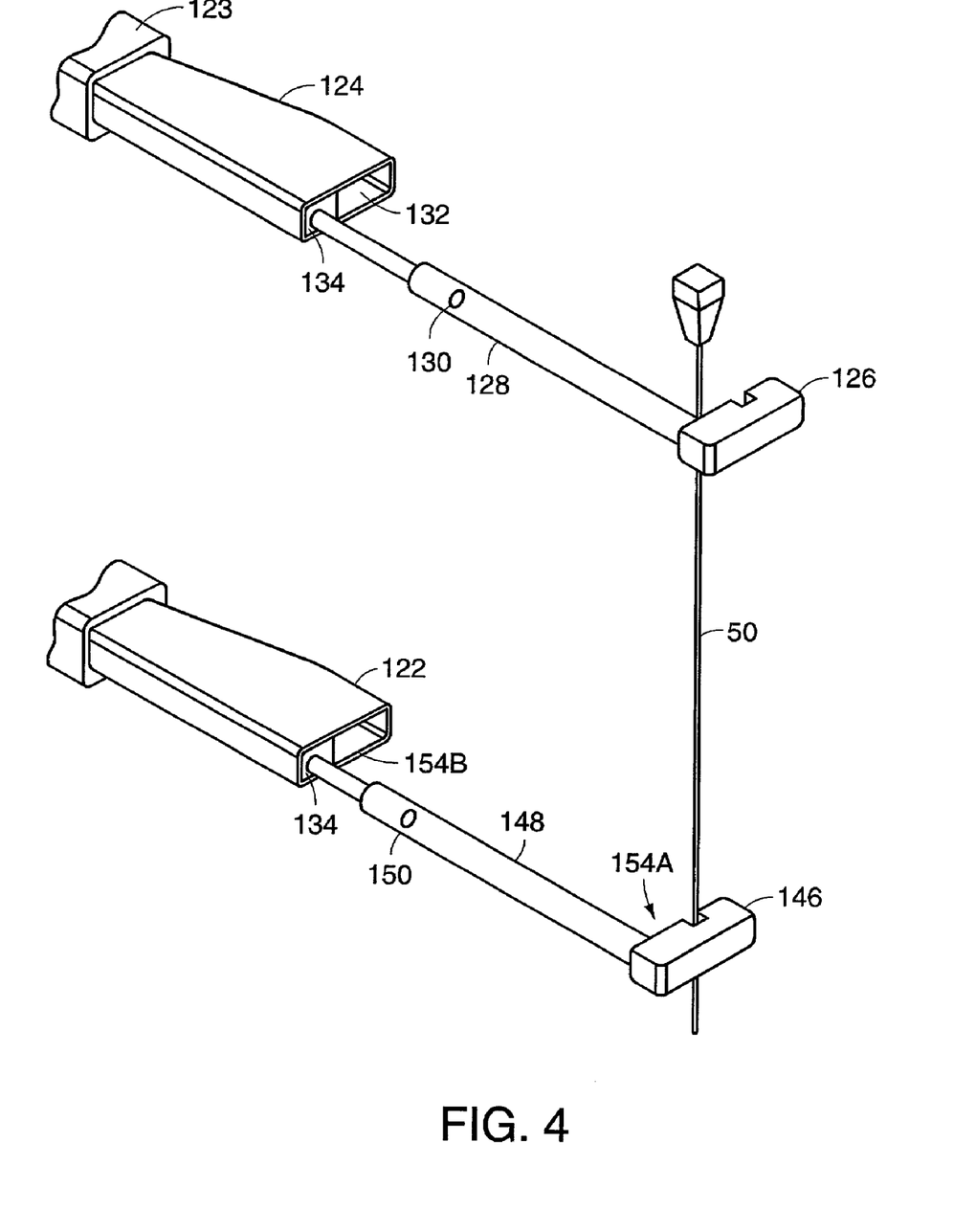
FIG. 4 is another perspective view of a portion of the penetrating driver of FIG. 2 illustrating removal of the release segment from the arms.

Thereafter, either or both of the releasable segments 126, 146 can be completely detached from the corresponding cantilevered part 124, 144 as shown in FIG. 4. This also allows the surgical personnel to replace the penetrating member/needle with another sterilized penetrating member/needle of the same or different size and replace the guide member 152 for the second arm 120, more particularly replace the guide member halves 154a,b in each of the releasable segment 146 and the cantilevered part 144 of the second arm.

Figure 6:
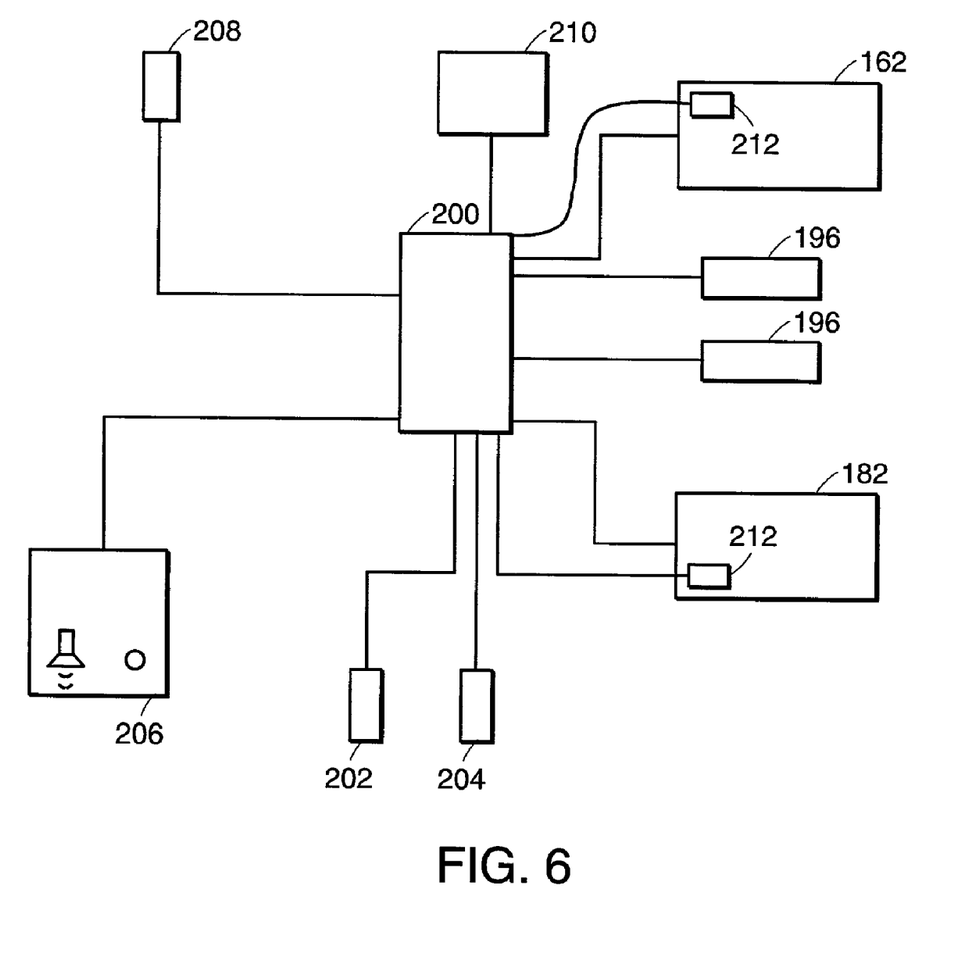
FIG. 6 is a block diagram of one scheme for controlling the driving of the penetrating member.

Now referring to FIG. 6 there is shown a schematic block diagram of a scheme or circuitry for controlling the operation of the motor 162 for the motorized translation transmission assembly 160, the motor 182 for the motorized rotational transmission assembly 180, and the solenoids 196 controlling the latch fingers 192 for each of the first and second arms 120, 140. The circuitry includes a controller 200, such as a microprocessor or digital signal processor as is known to those skilled in the art, configured and arranged so that various output signals are provided to any one of the motors 162, 182 or the solenoids responsive to certain input signals from sensors, switches or other input devices known to those skilled in the art.

Inputs are provided to the controller from one or more needle force sensor(s) 202, or one more needle vibration sensor(s). For example, a number of force sensors 202 can be arranged to provide three dimensional needle force sensing which can provide feedback to determine if the needle trajectory coincides with any obstructions. Also such force and vibration sensing can be utilized as a mechanism for sensing the presence of an anomalous condition or a possible anomalous condition that requires either of the rotational or translation motors 182, 162 to be stopped so the medical/surgical personnel can re-evaluate what is going on to determine if the protocol or technique being used to drive the penetrating member should be altered, modified or terminated. For example, the sensors could be set so that translation would be stopped when the sensors output signals to the controller 200 are determined to be of the type and magnitude that could be or is representative of a condition that might be indicating the presence of calcification or hard tissue.

When such a condition is detected, the controller also could output signals to a display/warning device 206 which would generate appropriate auditory and/or visual ques to draw the surgical/medical personnel's attention to the condition. The medical/surgical personnel responsive to these ques and additional information could then establish or utilize another needle driving protocol to deal with the changed condition using an input device 208 such as a conventional keyboard, mouse and/or or joystick. After establishing another needle driving protocol, the needle driving process would be re-started using the new protocol. It should be recognized that it is within the scope of the present invention for the controller to be configured and arranged so as to include a number of different needle driving protocols that can be accessed and used by the medical/surgical personnel.

In an additional embodiment, the controller 200 is configured and arranged so as to include a depth of penetration value inputted by the medical personnel for a given procedure. Because the translational motion of the first arm 120 is encoded, the spatial movement of the first arm as it translates is evaluated by the controller 200 to determine if the needle has penetrated within the body to the depth of penetration. If yes, then the controller 200 outputs signals to the motors 162, 182 stopping the needle driving process as well as outputting signals to generate auditory/visual ques to draw the personnel's attention to this stoppage.

In another embodiment, motor/motor power sensors 212 are provided to sense the operability of the motor and/or the availability of sufficient power of the right frequency, voltage and current to run a given motor. If the sensors indicate that such power is not available or that one or motors has undergone a catastrophic failure, then the controller can be configured and arranged to automatically shutdown the needle driving process and/or give an auditory/visual warning to the medical personnel. For example, if the rotational motor 182 failed and the translation motor remained operation, the controller 200 would output a signal calling for the translational motor 162 to be shut down.

In yet another embodiment, a switch 210 is provided that allows the medical personnel to manually shutdown the needle driving process and/or trigger/de-actuate the solenoids 196 so as to release the penetrating member/needle from the first and second arms 120, 140. For example, if the medical personnel saw the patient make a sudden movement or began coughing which could create a possibly unsafe condition if the needle 50 remained secured in the penetrating member driver 100, the surgical/medical personnel can trip the solenoids 196 to release the needle using the switch 210. Specifically, the switch 210 would output a signal to the controller 200 which in turn would trip the solenoids 196. The solenoids 196 also are preferably configured so that when there is a loss of power to the solenoids, the solenoids automatically de-actuate thereby releasing the needle 50.

Figure 7:
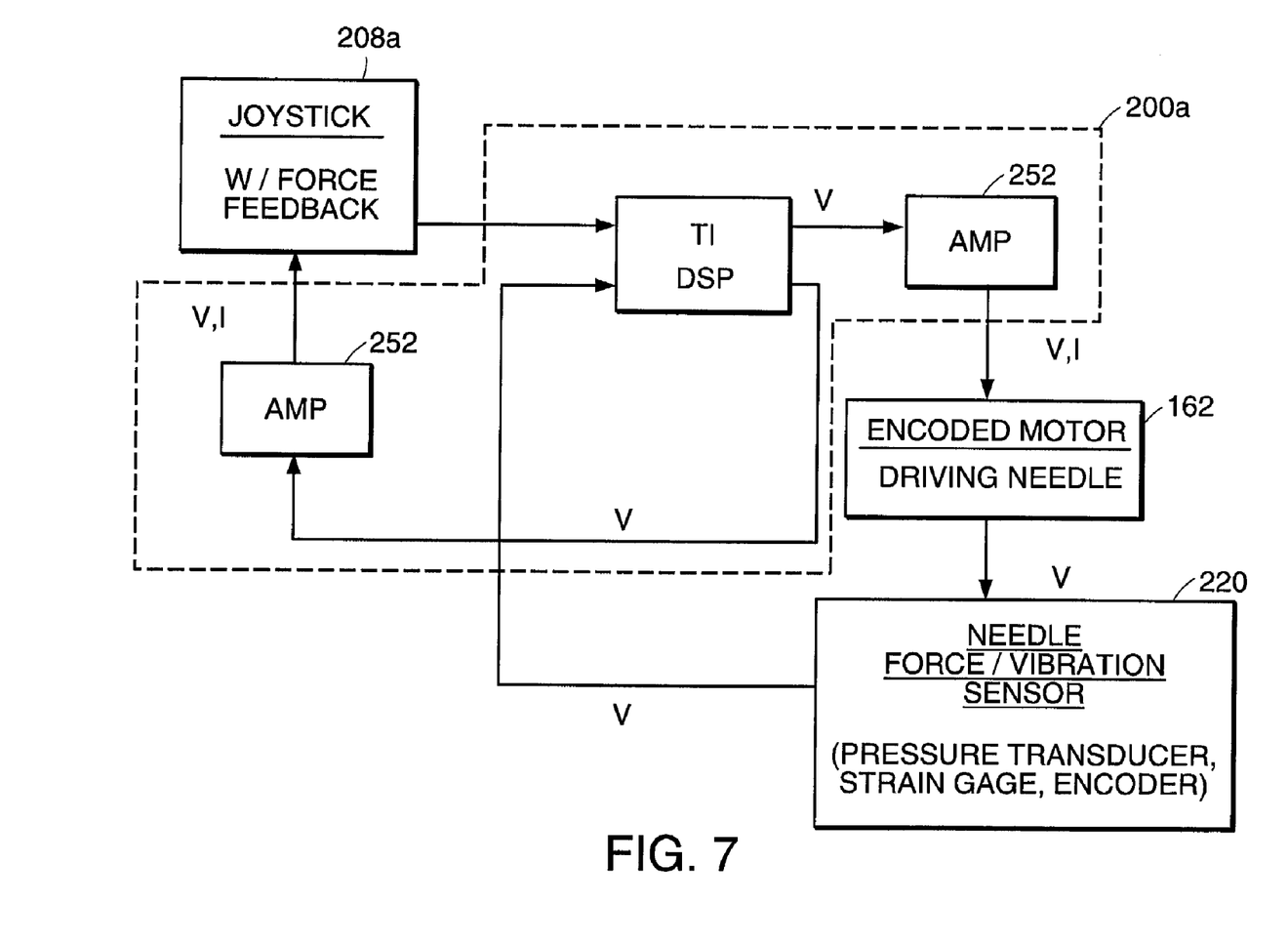
FIG. 7 is an exemplary circuit for controlling the translational driving of the penetrating member with a force feedback to the joystick.

There is shown in FIG. 7 a block diagram of another control circuit for controlling translation of the needle 50, which circuit also implements a force feedback to the joystick 208*a* that which is used to control or alter the ongoing needle driving process. In the illustrated embodiment, the controller 200*a* includes a digital signal processor 250, and two signal amplifiers 252 for amplifying signals to the translational motor 162 that control the direction of rotation as well as being capable of controlling the speed of rotation.

The needle force/vibration sensor 220, such as a pressure transducer, strain gauge or encoder, provides a signal output back to the DSP representative of the pressure/vibration being sensed. This output as described above is evaluated to determine if threshold values have been exceeded requiring termination of the needle driving process until the medical personnel can determine if this process can be restarted or continued, whether to change the needle driving protocol before restarting the needle driving process shutdown or whether to take some other appropriate action. Alternatively, the DSP could include instructions and criteria that allow the DSP to automatically alter or modify the needle driving protocol that was being implemented in accordance with some pre-established routine.

The needle force/vibration signals also are inputted back to the joystick as a force feedback from the DSP. As is known in the art, the joystick includes motors or mechanisms that can generate a back force on the joystick representative of a force. In the present invention, the force feedback from the DSP is representative of the force acting on the needle as it is being translated.

Although a preferred embodiment of the invention has been described using specific terms, such description is for illustrative purposes only, and it is to be understood that changes and variations may be made without departing from the spirit or scope of the following claims.

What is claimed is:

1. An apparatus for placing a proximal portion of a needle in a target area after the apparatus is positioned in proximity to an entry point of an object containing the target area by a manipulation device, the needle having a translational axis, said apparatus comprising:

a first arm being configured and arranged to rotatably support a distal portion of the needle about its translational axis;

a first drive mechanism being coupled to the first arm and being configured and arranged to translate the first arm from an initial position to any of a number of other positions spaced from the initial position, thereby also translating the needle along its translational axis in a direction towards the target area, wherein one of the any of a number of other positions corresponds to a condition where the needle proximal portion is disposed in the target area;

wherein the first arm and first drive mechanism are coupled to the manipulation device such that the manipulation device can position the apparatus in proximity to the entry point of the object containing the target area; and a second drive mechanism being coupled to the needle and being configured and arranged so as to cause the needle to rotate about translational axis of the needle; and a second arm spaced apart from the first arm, configured and arranged to support a proximal portion of the needle, said second arm being aligned with the first arm so that the first arm and distal portion of the needle are movable toward the second arm.

2. The apparatus of claim 1, wherein the first arm is operably coupled to the manipulation device that positions the first arm with respect to the entry point of the object containing the target area so a long axis of the needle passes through the target area.

3. The apparatus of claim 1, wherein the first drive mechanism is configured and arranged to translate the first arm so that the needle proximal portion moves along a translation axis that passes through the target area.

4. The apparatus of claim 1, wherein the second arm further includes a guide mechanism in which the needle is moveably received, and which is arranged and configured to restrain the movement of the needle to its translational axis.

5. An apparatus for placing a proximal portion of a needle in a target area, the needle having a translational axis, comprising:

a first arm being configured and arranged to rotatably support a distal portion of the needle about the translational axis of the needle;

a first drive mechanism being coupled to the first arm and being configured and arranged to translate the first arm from an initial position to any of a number of other positions spaced from the initial position, wherein one of the any of a number of other positions corresponds to a condition where the needle proximal portion is disposed in the target area;

wherein the first drive mechanism includes a linear guide that is configured and arranged so as to restrain motion of the first arm other than in the direction the first arm translates; and a second arm spaced apart from the first arm, configured and arranged to support a proximal portion of the needle, said second arm being aligned with the first arm so that the first arm and distal portion of the needle are movable toward the second arm.

6. The apparatus of claim 5, wherein the first arm is further configured and arranged to rotatably support the needle about the translational axis of the needle; and wherein the apparatus further comprises:

a second drive mechanism being coupled to the needle and being configured and arranged so as to cause the needle to rotate about the translational axis of the needle.

7. The apparatus of claim 6, wherein the first and second drive mechanisms are configured and arranged so that translating of the first arm and rotating of the needle are separately and independently controlled.

8. The apparatus of claim 6, wherein the first and second drive mechanisms are configured and arranged so that translating of the first arm and rotating of the needle are performed at the same time.

9. The apparatus of claim 6, wherein the first and second drive mechanisms are configured and arranged so as to do one of translating of the first arm or rotating of the needle.

10. The apparatus of claim 6, wherein the second drive mechanisms is configured and arranged so as to selectively rotate the needle at one of a number of different rotational speeds.

11. The apparatus of claim 6, further comprising:

a controller that is configured and arranged to selectively and separately control the first and second drive mechanisms.

12. The apparatus of claim 11, wherein the controller is further configured so as to include a plurality of pre-established needle driving protocols for driving the needle end portion from an initial position to the target area.

13. The apparatus of claim 11, wherein the controller is configured and arranged so that translating of the first arm and rotating of the needle are performed at the same time.

14. The apparatus of claim 11, wherein the controller is configured and arranged so as to do one of translating of the first arm or rotating of the needle.

15. The apparatus of claim 11, wherein the controller is configured and arranged so as to selectively rotate the needle at one of a number of different rotational speeds.

16. The apparatus of claim 11, wherein the controller is configured and arranged so as to successively translate the needle in a back and forth manner.

17. The apparatus of claim 11 further comprising a sensor and wherein the controller is configured and arranged to alter the needle driving protocol based on signals from the sensor.

18. The apparatus of claim 5, wherein the second arm is coupled to the first drive mechanism so that the first arm translates towards the second arm.

19. The apparatus of claim 18, in which the second arm further includes a guide mechanism in which the needle is moveably received.

20. The apparatus of claim 19, wherein the guide mechanism is selectively configurable so as to be capable of guiding differently sized needles.

21. The apparatus of claim 18, wherein the second arm includes a detachable portion and a latching mechanism configured so as to releasably secure the detachable portion to a rest of the second arm.

22. The apparatus of claim 21 wherein the detachable portion includes at least a portion of a guide mechanism in which the needle is moveably received.

23. The apparatus of claim 5, wherein the first arm includes a detachable portion and a latching mechanism configured so as to releasably secure the detachable portion to a rest of the first arm.

24. The apparatus of claim 5, wherein the first drive mechanisms includes a slipless transmission assembly.

25. The apparatus of claim 5, wherein the first drive mechanism comprises a screw mechanically coupled to the first arm such that rotation of the screw causes the first arm to translate from the first position.

26. The apparatus of claim 25, wherein the first drive mechanism further includes a bi-directional motor coupled to the screw and wherein the first arm can be translated in one of two direction responsive to the direction of rotation of the motor.

27. The apparatus of claim 5, wherein the linear guide comprises:

a rod member;

a track;

a sliding member a portion of which is configured to slidably engaged the track and which is secured to the first arm; and a coupling mechanism secured to the sliding member and slidably coupling the rod member to the sliding member.

28. The apparatus of claim 5, wherein the needle is configured so as to be capable of performing any one of injecting therapeutic agents into the target area, locating an imaging device in the target area, biopsy including tissue biopsy, and locating a medical device in the target area to be used to perform an medical procedure.

29. An apparatus for placing a proximal portion of a needle in a target area after the apparatus is positioned in proximity to an entry point of an object containing the target area, the needle having a translational axis, said apparatus comprising:

a first arm being configured and arranged to rotatably support the needle about the translational axis of the penetrating member;

a first drive mechanism being coupled to the first arm and being configured and arranged to translate the first arm from an initial position to any of a number of other positions spaced from the initial position, thereby also translating the needle along its translational axis in a direction towards the target area, wherein one of the any of a number of other positions corresponds to a condition where the needle proximal portion is disposed in the target area;

a second drive mechanism being coupled to the needle and being configured and arranged so as to cause the needle to rotate about the translational axis of the needle; and wherein the second drive mechanism comprises a gear member secured to the needle and being mechanically coupled to a motor such that operation of the motor causes the needle to rotate about its translational axis.

30. An apparatus for placing a proximal portion of a needle in a target area after the apparatus is positioned in proximity to an entry point of an object containing the target area, the needle having a translational axis, said apparatus comprising:

a first arm being configured and arranged to rotatably support a distal portion of the needle about the translational axis of the needle;

a first drive mechanism being coupled to the first arm and being configured and arranged to translate the first arm from an initial position to any of a number of other positions spaced from the initial position, thereby also translating the needle proximal portion in a direction towards the target area, wherein one of the any of a number of other positions corresponds to a condition where the needle proximal portion is disposed in the target area;

wherein the first drive mechanism includes a linear guide that is configured and arranged so as to restrain motion of the first arm other than in the direction the first arm translates;

a second arm spaced apart from the first arm, configured and arranged to support a proximal portion of the needle, and coupled to the first drive mechanism so that the first arm translates towards the second arm; and a second drive mechanism being coupled to the needle and being configured and arranged so as to cause the needle to rotate about the translational axis of the needle.

31. The apparatus of claim 30 wherein the first and second drive mechanisms are configured and arranged so that translating of the first arm and rotating of the needle are separately and independently controlled.

32. The apparatus of claim 30, wherein the first and second drive mechanisms are configured and arranged so that translating of the first arm and rotating of the needle are performed at the same time.

33. The apparatus of claim 30, wherein the first and second drive mechanisms are configured and arranged so as to do one of translating of the first arm or rotating of the needle.

34. The apparatus of claim 30, wherein the second drive mechanisms is configured and arranged so as to selectively rotate the needle at one of a number of different rotational speeds.

35. The apparatus of claim 30, in which the second arm further includes a guide mechanism in which the needle is moveably received.

36. The apparatus of claim 30, wherein:

the first arm includes a detachable portion and a latching mechanism configured so as to releasably secure the detachable portion to a rest of the first arm; and the second arm includes a detachable portion and a latching mechanism configured so as to releasably secure the detachable portion to a rest of the second arm.

37. The apparatus of claim 30, wherein the first drive mechanism comprises:

a screw mechanically coupled to the first arm such that rotation of the screw causes the first arm to translate from the first position;

a bi-directional motor coupled to the screw; and wherein the first arm is translated in one of two direction responsive to the direction of rotation of the motor.

38. The apparatus of claim 30, wherein the linear guide comprises:

a rod member;

a track;

a sliding member a portion of which is configured to slidably engaged the track and which is secured to the first arm; and a coupling mechanism secured to the sliding member and slidably coupling the rod member to the sliding member.

39. The apparatus of claim 30, further comprising a controller that is configured and arranged to selectively and separately control the first and second drive mechanisms.

40. The apparatus of claim 30, wherein the first arm is operably coupled to an apparatus that positions the first arm with respect to the entry point of the object containing the target area so a long axis of the needle passes through the target area.

41. The apparatus of claim 30, wherein the first drive mechanism is configured and arranged to translate the first arm so that the penetrating member proximal portion moves along a translation axis that passes through the target area.

42. An apparatus for driving a subcutaneous needle so a proximal portion thereof is located in a target area of a body after the apparatus is positioned in proximity to an entry point of the body, the needle having a translational axis, said apparatus comprising:

a first arm being configured and arranged to rotatably support the needle about the translational axis of the needle;

a first drive mechanism being coupled to the first arm and being configured and arranged to translate the first arm from an initial position to any of a number of other positions spaced from the initial position, thereby also translating the needle proximal portion in a direction towards the target area, wherein one of the any of a number of other positions corresponds to a condition where the needle proximal portion is disposed in the target area;

a second arm coupled to the first drive mechanism so that the first arm translates towards the second arm;

wherein the first drive mechanism includes a linear guide that is configured and arranged so as to restrain motion of the first arm other than in the direction the first arm translates;

a second drive mechanism being coupled to the needle and being configured and arranged so as to cause the needle to rotate about the translational axis of the needle; and wherein the second arm further includes a guide mechanism in which the needle is moveably received.

43. The apparatus of claim 42, wherein:

the first arm includes a detachable portion and a latching mechanism configured so as to releasably secure the detachable portion to a rest of the first arm; and the second arm includes a detachable portion and a latching mechanism configured so as to releasably secure the detachable portion to a rest of the second arm.

44. The apparatus of claim 42, wherein the first arm is operably coupled to an apparatus that positions the first arm with respect to the entry point of the object containing the target area so a long axis of the needle passes through the target area.

45. The apparatus of claim 42, wherein the first drive mechanism is configured and arranged to translate the first arm so that the needle moves along a translation axis that passes through the target area.

46. An apparatus for driving a subcutaneous needle so a proximal portion thereof is located in a target area of a body after the apparatus is positioned in proximity to an entry point of the body, said apparatus comprising:

a first arm being configured and arranged to rotatably support the needle about the translational axis of the needle;

a first drive mechanism being coupled to the first arm and being configured and arranged to translate the first arm from an initial position to any of a number of other positions spaced from the initial position, thereby also translating the penetrating member proximal portion in a direction towards the target area, wherein one of the any of a number of other positions corresponds to a condition where the needle proximal portion is disposed in the target area;

a second arm coupled to the first drive mechanism so that the first arm translates towards the second arm;

a second drive mechanism being coupled to the needle and being configured and arranged so as to cause the needle to rotate about the translational axis of the needle;

wherein the second arm further includes a guide mechanism in which the needle is moveably received; and wherein the first drive mechanism comprises:

a screw mechanically coupled to the first arm such that rotation of the screw causes the first arm to translate from the first position;

a bi-directional motor coupled to the screw;

wherein the first arm is translated in one of two direction responsive to the direction of rotation of the motor; and a linear guide that is configured and arranged so as to restrain motion of the first arm other than in the direction the first arm translates, wherein the linear guide includes:

a rod member, a track, a sliding member a portion of which is configured to slidably engaged the track and which is secured to the first arm, and a coupling mechanism secured to the sliding member and slidably coupling the rod member to the sliding member.

47. An apparatus for driving a subcutaneous needle so a proximal portion thereof is located in a target area of a body after the apparatus is positioned in proximity to an entry point of the body, said apparatus comprising:

a first arm being configured and arranged to rotatably support the needle about the translational axis of the needle;

a first drive mechanism being coupled to the first arm and being configured and arranged to translate the first arm from an initial position to any of a number of other positions spaced from the initial position, thereby also translating the penetrating member proximal portion in a direction towards the target area, wherein one of the any of a number of other positions corresponds to a condition where the needle proximal portion is disposed in the target area;

a second arm coupled to the first drive mechanism so that the first arm translates towards the second arm;

a second drive mechanism being coupled to the needle and being configured and arranged so as to cause the needle to rotate about the translational axis of the needle;

wherein the second arm further includes a guide mechanism in which the needle is moveably received; and wherein the second drive mechanism comprises:

a gear member secured to the penetrating member;

a drive gear that is mechanically coupled to the motor and the penetrating member gear member so that the penetrating member gear member rotates responsive to rotation of the motor;

wherein the motor is a bi-directional motor; and wherein the penetrating member can be rotated in one of a clockwise and counter clockwise direction responsive to the direction of rotation of the motor.

48. A method for localizing a proximal portion of a needle in a target area of a body, the needle having a translational axis, comprising the steps of:

supporting a distal portion of the needle from a first arm and a proximal portion of the needle from a second arm;

positioning the first arm and second arm with respect to the body so the translational axis of the needle passes through the target area;

linearly translating the first arm from an initial position to any of a number of other positions spaced from the initial position, thereby also translating the needle proximal portion in a direction towards the target area, wherein one of the any of a number of other positions corresponds to a condition where the needle proximal portion is disposed in the target area; and rotating the needle about the translational axis of the needle.

49. The method of claim 48, wherein said steps of rotating said needle and translating the first arm are concurrently performed as the needle proximal portion is translated through a surface of the body.

50. An apparatus for placing a proximal portion of a penetrating member in a target area after the apparatus is positioned in proximity to an entry point of an object containing the target area, the penetrating member having a translational axis, said apparatus comprising:

a first arm being configured and arranged to rotatably support the penetrating member about the translational axis of the penetrating member;

a first drive mechanism being coupled to the first arm and being configured and arranged to translate the first arm from an initial position to any of a number of other positions spaced from the initial position, thereby also translating the penetrating member along its translational axis in a direction towards the target area, wherein one of the any of a number of other positions corresponds to a condition where the penetrating member proximal portion is disposed in the target area;

a second drive mechanism being coupled to the penetrating member and being configured and arranged so as to cause the penetrating member to rotate about the translational axis of the penetrating member; and wherein the second drive mechanism comprises a gear member secured to the penetrating member and being mechanically coupled to a motor such that operation of the motor causes the penetrating member to rotate about its translational axis, wherein the second drive mechanism further includes a drive gear that is mechanically coupled to the motor and the penetrating member gear member so that the penetrating member gear member rotates responsive to rotation of the drive gear.

51. The apparatus of claim 50, wherein the motor is a bi-directional motor and wherein the penetrating member can be rotated in one of a clockwise and counter clockwise direction responsive to the direction of rotation of the motor.

52. An apparatus for placing a proximal portion of a penetrating member in a target area after the apparatus is positioned in proximity to an entry point of an object containing the target area, the penetrating member having a translational axis, said apparatus comprising:
- a first arm being configured and arranged to rotably support the penetrating member about the translational axis of the penetrating member;
- a first drive mechanism being coupled to the first arm and being configured and arranged to translate the first arm from an initial position to any of a number of other positions spaced from the initial position, thereby also translating the penetrating member proximal portion in a direction towards the target area, wherein one of the any of a number of other positions corresponds to a condition where the penetrating member proximal portion is disposed in the target area;
- wherein the first drive mechanism includes a linear guide that is configured and arranged so as to restrain motion of the first arm other than in the direction the first arm translates;
- a second arm coupled to the first drive mechanism so that the first arm translates towards the second arm; and
- a second drive mechanism being coupled to the penetrating member and being configured and arranged so as to cause the penetrating member to rotate about the translational axis of the penetrating member,
- the second drive mechanism comprising a gear member secured to the penetrating member, and a drive gear that is mechanically coupled to a motor and the penetrating member gear member so that the penetrating member gear member rotates responsive to rotation of the motor.

53. The apparatus of claim 52, wherein the motor is a bi-directional motor and wherein the penetrating member can be rotated in one of a clockwise and counter clockwise direction responsive to the direction of rotation of the motor.

54. An apparatus for placing an end of an elongated tissue penetrating needle into a target area by longitudinal translation of the tissue penetrating needle in a desired travel path comprising:
- a first arm arranged and configured to grasp a distal portion of the tissue penetrating needle;
- a first drive mechanism coupled to the first arm and arranged and configured to translate the first arm from an initial position to a secondary position toward the target area, thereby also longitudinally translating the tissue penetrating needle toward the target area; and
- a second arm spaced apart from the first arm, arranged and configured to support a proximal portion of the tissue penetrating needle, said second arm including a guide mechanism in which the tissue penetrating needle is moveably received, and which is arranged and configured to restrain the movement of the tissue penetrating needle to translation along its longitudinal axis.

55. The apparatus of claim 54, wherein the first and second arms are configured and arranged such that the first arm and distal portion of the tissue penetrating needle translate toward the second arm.

56. The apparatus of claim 54, further comprising a second drive mechanism coupled to the tissue penetrating needle, and arranged and configured to cause the tissue penetrating needle to rotate about the translational axis of the tissue penetrating needle.

57. The apparatus of claim 56, wherein the second drive mechanism comprises a first motor-driven gear member coupled to a second gear member secured to the tissue penetrating needle, causing the tissue penetrating needle to rotate about its translational axis in response to rotation of the motor.

* * * * *